US009011366B2

(12) United States Patent
Dean et al.

(10) Patent No.: US 9,011,366 B2
(45) Date of Patent: Apr. 21, 2015

(54) WICK AND RELIEF VALVE FOR DISPOSABLE LAPAROSCOPIC SMOKE EVACUATION SYSTEM

(75) Inventors: Robert O. Dean, Buffalo, NY (US); Jay T. Kajdas, Getzville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 1382 days.

(21) Appl. No.: 12/529,503

(22) PCT Filed: Feb. 29, 2008

(86) PCT No.: PCT/US2008/002759
§ 371 (c)(1),
(2), (4) Date: Sep. 1, 2009

(87) PCT Pub. No.: WO2008/109014
PCT Pub. Date: Sep. 12, 2008

(65) Prior Publication Data
US 2010/0094200 A1    Apr. 15, 2010

Related U.S. Application Data

(60) Provisional application No. 60/904,270, filed on Mar. 1, 2007.

(51) Int. Cl.
*A61M 37/00* (2006.01)
*A61B 18/00* (2006.01)
*B01D 46/00* (2006.01)
*B01D 46/10* (2006.01)

(52) U.S. Cl.
CPC .......... *A61B 18/00* (2013.01); *A61B 2218/008* (2013.01); *B01D 46/0036* (2013.01); *B01D 46/10* (2013.01)

(58) Field of Classification Search
CPC ..................... A61B 18/00; A61B 2218/008
USPC ................. 604/23–26, 131, 19, 536
See application file for complete search history.

(56) References Cited

U.S. PATENT DOCUMENTS

| 6,220,299 B1* | 4/2001 | Arvidsson et al. ............ 137/863 |
| 6,544,210 B1* | 4/2003 | Trudel et al. .................... 604/26 |
| 2001/0014139 A1* | 8/2001 | Price et al. ..................... 378/130 |
| 2003/0024528 A1* | 2/2003 | Graham .................. 128/201.13 |
| 2005/0000196 A1* | 1/2005 | Schultz ........................ 55/385.2 |
| 2005/0137577 A1* | 6/2005 | Heruth et al. ................. 604/536 |

OTHER PUBLICATIONS

ISA/US, International Search Report for PCT/US2008/002759, Sep. 19, 2008.
ISA/US, Written Opinion of the International Searching Authority for PCT/US2008/002759, Sep. 19, 2008.

* cited by examiner

*Primary Examiner* — Kevin C Sirmons
*Assistant Examiner* — Phillip Gray
(74) *Attorney, Agent, or Firm* — Phillips Lytle LLP (57) ABSTRACT

The present invention relates to an improved smoke evacuation device for use in laparoscopic surgeries. One improvement is a hydrophilic wick positioned within the inlet system of the smoke device for absorbing moisture and trapping surgical waste entering the smoke evacuation device. The second improvement is a multi-outlet valve inserted into the outlet system of the smoke evacuation device to enable quick depressurization of the surgical site.

17 Claims, 9 Drawing Sheets

Fig. 1

PRIOR ART

WICK AND RELIEF VALVE FOR DISPOSABLE LAPAROSCOPIC SMOKE EVACUATION SYSTEM

CROSS REFERENCE TO RELATED PATENT APPLICATION

This application claims the priority benefit of U.S. Provisional Patent Application No. 60/904,270, filed Mar. 1, 2007.

FIELD OF THE INVENTION

The invention relates to surgical procedures and, more specifically, to a device for more efficiently removing surgical waste and vapor smoke-free environment within the surgical field during laparoscopy.

BACKGROUND OF THE INVENTION

Laparoscopy is a fast growing surgical modality widely used in the treatment of certain prevalent physical ailments. Laparoscopy entails the introduction of an endoscope, light source, and surgical instruments through ports formed in the patient's abdomen. In order to facilitate the procedure, the patient's abdominal cavity is inflated with a suitable gas typically $CO_2$ to give the surgeon additional working area and minimize obstruction. Generally, laparoscopy avoids the risks of laparotomy, which requires the surgeon to open the abdomen and carry out the required procedure by his or her direct viewing.

However, when the laparoscopic procedure requires tissue removal by ablation, several channels through the abdominal wall are required. These include a channel for the laparoscopic camera needed for viewing the surgical field, a channel for the laser or electrosurgical instrument used to burn the target tissue, a channel for insufflation (introduction of $CO_2$ gas into the patient's cavity to expand the patient's cavity) with $CO_2$ gas, and a means for withdrawal of gas and smoke. Note that insufflation with a suitable gas is required during the laparoscopic procedure so as to provide both increased cavity volume and optimal visual conditions during the surgical procedure. A smoke clearing system is usually employed in order to maintain both the visual clarity and proper abdominal pressure within the expanded cavity during the procedure.

A common procedure for positioning the laparoscopic assembly in the patient's abdominal cavity includes first making an incision into the patient's abdominal wall through which a large gauge needle is inserted. A suitable gas, typically $CO_2$, is then introduced into the patient's abdominal cavity through the needle. The needle is then replaced with a trocar, which is then removed leaving behind a sleeve, or cannula, through which a laparoscope is introduced into the abdominal cavity. In order to perform laser or electrosurgery one or two additional small incisions are made in the abdominal wall over the surgical site and cannula/trocar assemblies positioned accordingly. These cannula/trocar assemblies may be used for the positioning of the insufflation tube as well as any other surgical instruments that may be required for the particular laparoscopic procedure.

A laparoscopic procedure typically requires a surgeon to employ either electrosurgery or laser surgery within the confined space of the patient's abdominal cavity. This surgery typically involves tissue burning or ablation. This tissue burning leads to the creation of smoke. Surgical smoke within the confines of a patient's abdominal cavity reduces the surgeon's view of the surgical site, increases the patient's hematocrit levels, and causes delays in the surgery while the smoke is cleared from the laparoscopic field. Efficient removal of the smoke is thus a necessity for the surgical team during the laparoscopic procedure.

Although a laparoscopic evacuation system ("lapevac system") is effective in maintaining cavity inflation pressure, one problem that occurs during its operation is the clogging of the inlet tube and filter by solid waste, water and humidity carried out of the abdominal cavity by the incoming waste stream. Because the cavity is moist and may be heated above normal temperature by some surgical procedures such as cauterization, surgical wastes can be driven off the cavity wall and internal organs in the form of particles, vapor, and liquids from broken cells and tissues. In addition, vapors within the cavity itself can be drawn into the waste stream. Another problem that may occur during laparoscopic surgery is the insufficient removal of waste vapor from the cavity, stratification of water vapor in the cavity as well as other visualization problems.

Therefore, there is a need in the field for an improved laparoscopic surgical system that is designed to prevent clogging of the inlet and filter by surgical waste and that will reduce or eliminate stratification of smoke and water vapor in the abdominal cavity during laparoscopic surgery

SUMMARY OF THE INVENTION

The present invention is an improvement of a laparoscopic surgical device that comprises a smoke removal apparatus having a housing, inlet means for defining an inlet pathway for impure gas from a surgical cavity to the housing, wherein the inlet means includes locking means for connecting the surgical cavity to the inlet pathway, filter means for filtering impurities from impure gas to form filtered gas, outlet means for defining an outlet pathway for the filtered gas from the housing to the surgical cavity, and a fan for drawing impure gas from the surgical cavity through the inlet means and through the filter means to form the filtered gas and for driving the filtered gas through the outlet means into the surgical cavity, wherein the outlet means are adapted to a laparoscopic surgical instrument assembly, the improvement comprising a hydrophilic wick inserted into and attached to the locking means of the inlet means.

In a separate improvement, the improvement to the smoke removal apparatus comprises a multi-outlet valve incorporated into the outlet means.

In an additional embodiment, the improvement to the smoke removal apparatus comprises both a hydrophilic wick inserted into and attached to the inlet means and a multi-outlet valve incorporated into the outlet means.

One object of the present invention is to reduce or eliminate blocking of the inlet means by surgical waste.

A second object of the present invention is reduce or eliminate stratification of surgical smoke and water vapor in the abdominal cavity by supplying a venting valve on the outlet means of the surgical smoke removal device to effect quick removal of smoke and water vapor.

BRIEF DESCRIPTION OF THE DRAWINGS

The nature and mode of operation of the present invention will now be more fully described in the following detailed description of the invention taken with the accompanying drawing figures, in which:

FIG. 8A is a top view of a second embodiment of the two-way outlet divert valve in the off mode;

FIG. 8B is a top view of the second embodiment of the two-way outlet valve in the open mode; and, FIG. 8C is a top view of the second embodiment of the two-way outlet valve in the divert mode.

DETAILED DESCRIPTION OF THE INVENTION

At the outset, it should be appreciated that like drawing numbers on different drawing views identify identical structural elements of the invention. While the present invention is described with respect to what is presently considered to be the preferred embodiments, it is understood that the invention is not limited to the disclosed embodiment.

Furthermore, it is understood that this invention is not limited to the particular methodology, materials and modifications described and as such may, of course, vary. It is also understood that the terminology used herein is for the purpose of describing particular embodiments only, and is not intended to limit the scope of the present invention.

Figure 1:
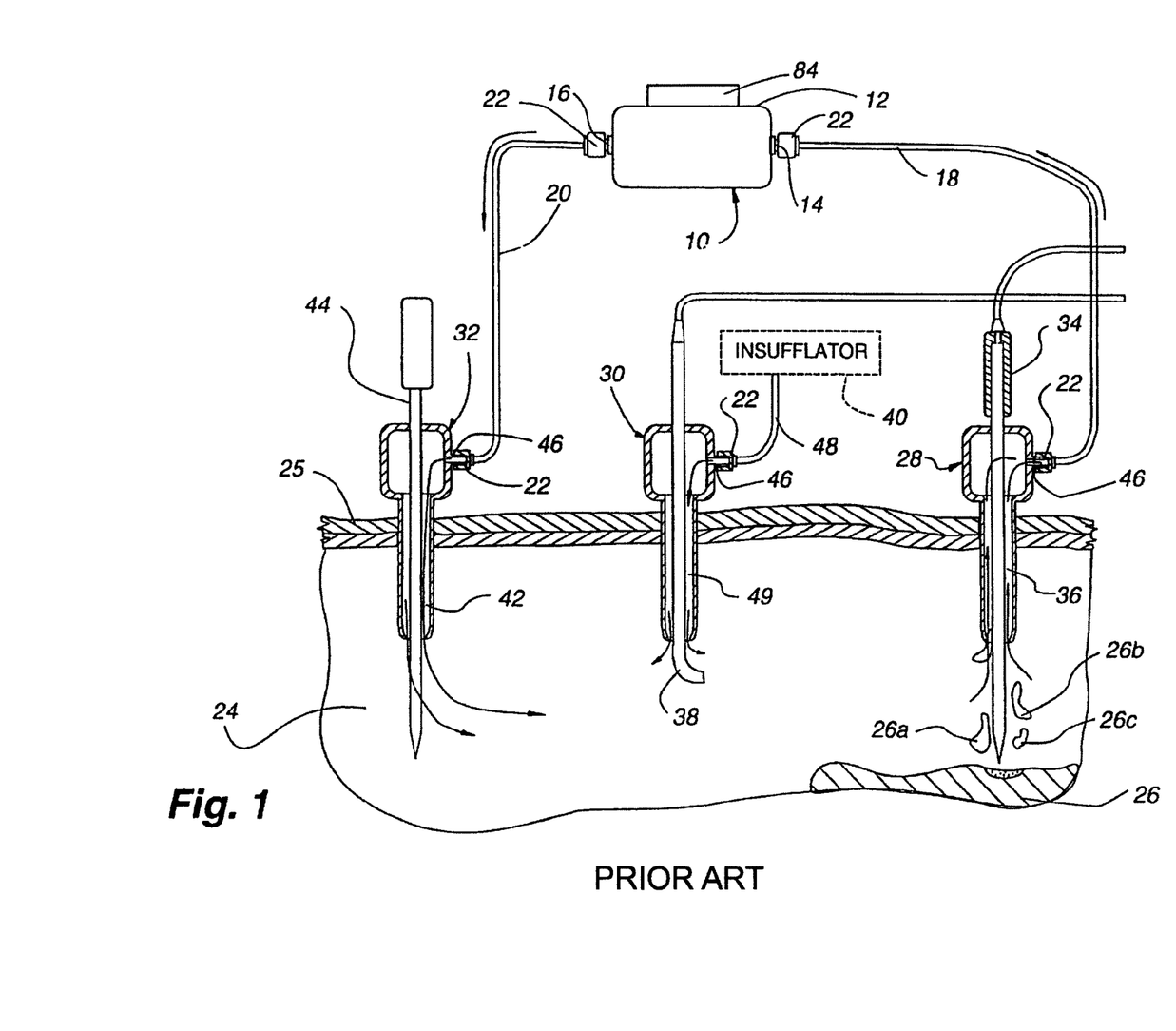
FIG. 1 is a schematic view of a laparoscopic smoke evacuation system of the prior art depicting the arrangement of the smoke evacuation system during laparoscopic surgery.

Adverting now to the figures, FIG. 1 is a schematic view of a laparoscopic smoke evacuation system of the prior art depicting the arrangement of the smoke evacuation system during laparoscopic surgery. Smoke clearing device 10 includes housing 12. Housing 12 may be made out of a variety of materials, such as a metal or a plastic, as long as the material facilitates the device's use and is preferably disposable. The housing 12 preferably has a generally rectangular box shape or it may have a generally cylindrical hollow shape, preferably with rounded corners. The housing 12 contains an inlet port 14 at one end, i.e., on one side and an outlet port 16 at the other end, i.e., on the opposite side. One end of an inlet tube 18 is connected to the inlet port 14. One end of an outlet tube 20 is connected to the outlet port 16. This tubing is preferably conventional sterile flexible plastic tubing. It is envisioned that conventional Luer lock structures 22 will be used to connect the tubes 18 and 20 to the housing 12, but other locking structures could alternatively be used.

The patient's inner cavity, such as the abdominal cavity, is shown as 24 and the patient's skin is schematically shown as 25 in FIG. 1. The patient's tissue which is to be removed is shown as 26, with the surgical smoke shown and indicated as 26a, 26b, and 26c. Three trocars containing laparoscopic surgical instrument clusters 28, 30 and 32 extend through the patient's skin 25 into the cavity 24.

These groups of instruments are representative of the type of instruments that are typically used in laparoscopic surgery. Each instrument cluster includes a cannula/trocar for introducing the instrument into the patient's cavity and maintaining a seal to the cavity 24 to preclude gas escape from the cavity 24. Each cannula/trocar has a single channel or passage along its length that allows instruments to be inserted into the body while maintaining the intra-abdominal pressure created by insufflation. Instrument cluster 28 is a single channel instrument cluster which serves to house the laser instrument 34 and direct the laser beam to the operating site. An annular channel 36 around the instrument 34 within the trocar serves as an annular egress passage from near the operating site for gas to be drawn around the laser instrument 34 and out of the patient's cavity to the smoke clearing device 10 of the present invention.

Figure 2:
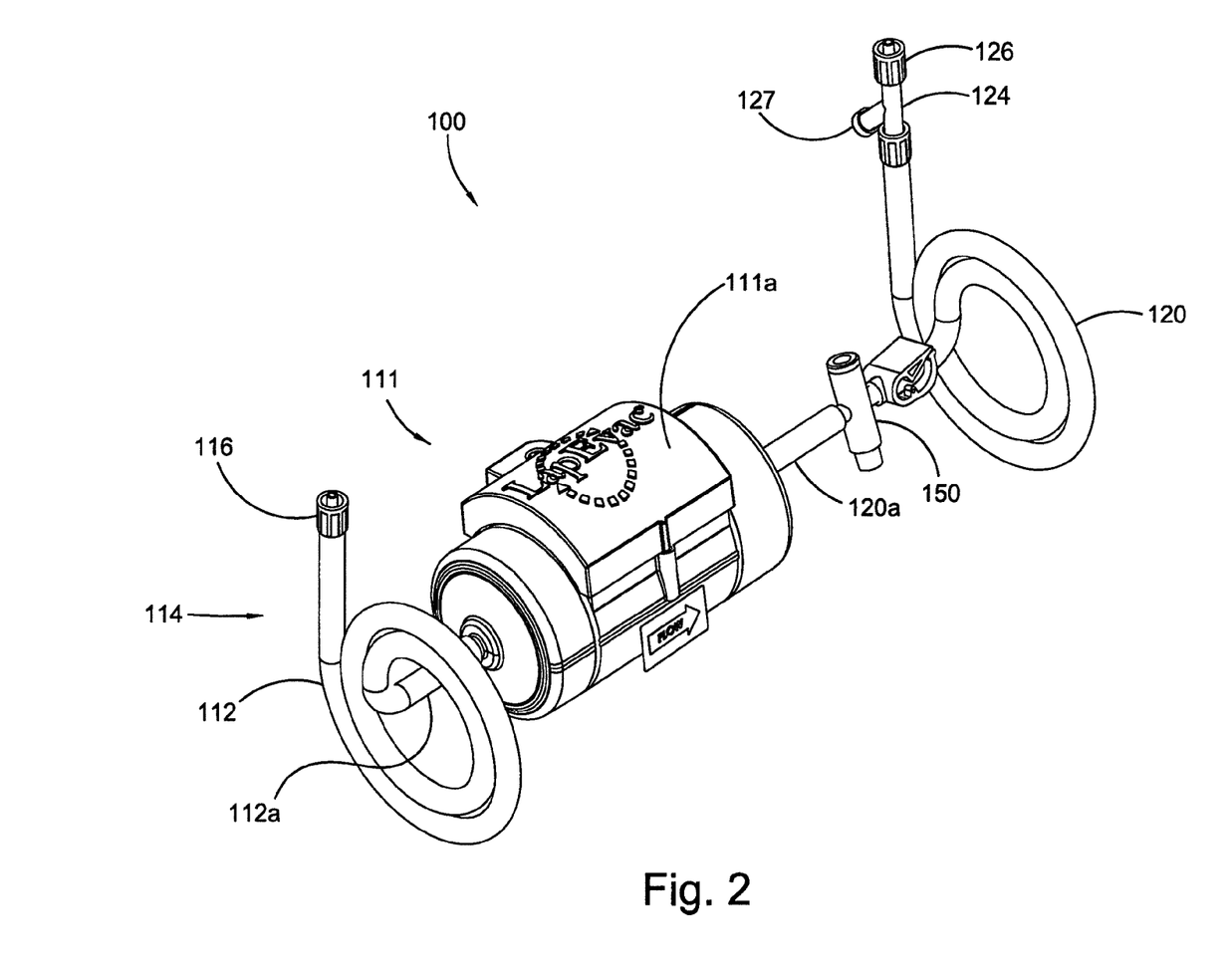
FIG. 2 is a top perspective view of a typical disposable laparoscopic smoke evacuation system with the improvements of the present invention.

FIG. 2 is a top perspective view of a typical disposable laparoscopic smoke evacuation system 100 ("lapevac 100"). Such devices are described in U.S. Pat. No. 6,544,210 to Trudel, et al. which is hereby incorporated by reference in its entirety. Housing 111 is shown with inlet means, in this case inlet tube 112 and outlet means, in this case outlet tube 120 attached to inlet attachment 112a and outlet attachment 120a, respectively. Inserted into the input end of inlet tube 112 is wick assembly 114. Attached to the outlet attachment 120a is the inlet of one embodiment of a multi-outlet relief valve, in this case a two-way bleed or relief valve, t-tap valve 150. By two-way valve is meant a valve that has at least two outlets that allow material, such as a gas or liquid fluid, that enters the valve to be directed to one of two or more different outlet flow paths. Also seen is y-connector 124 ("connector 124") at the end of outlet tube 120. Persons of skill in the art will recognize that the two-way valves may be connected to outlet tube 120 in any convenient position within the length of outlet tube 120 and that valves having more than two outlets may also be used.

Figure 3:
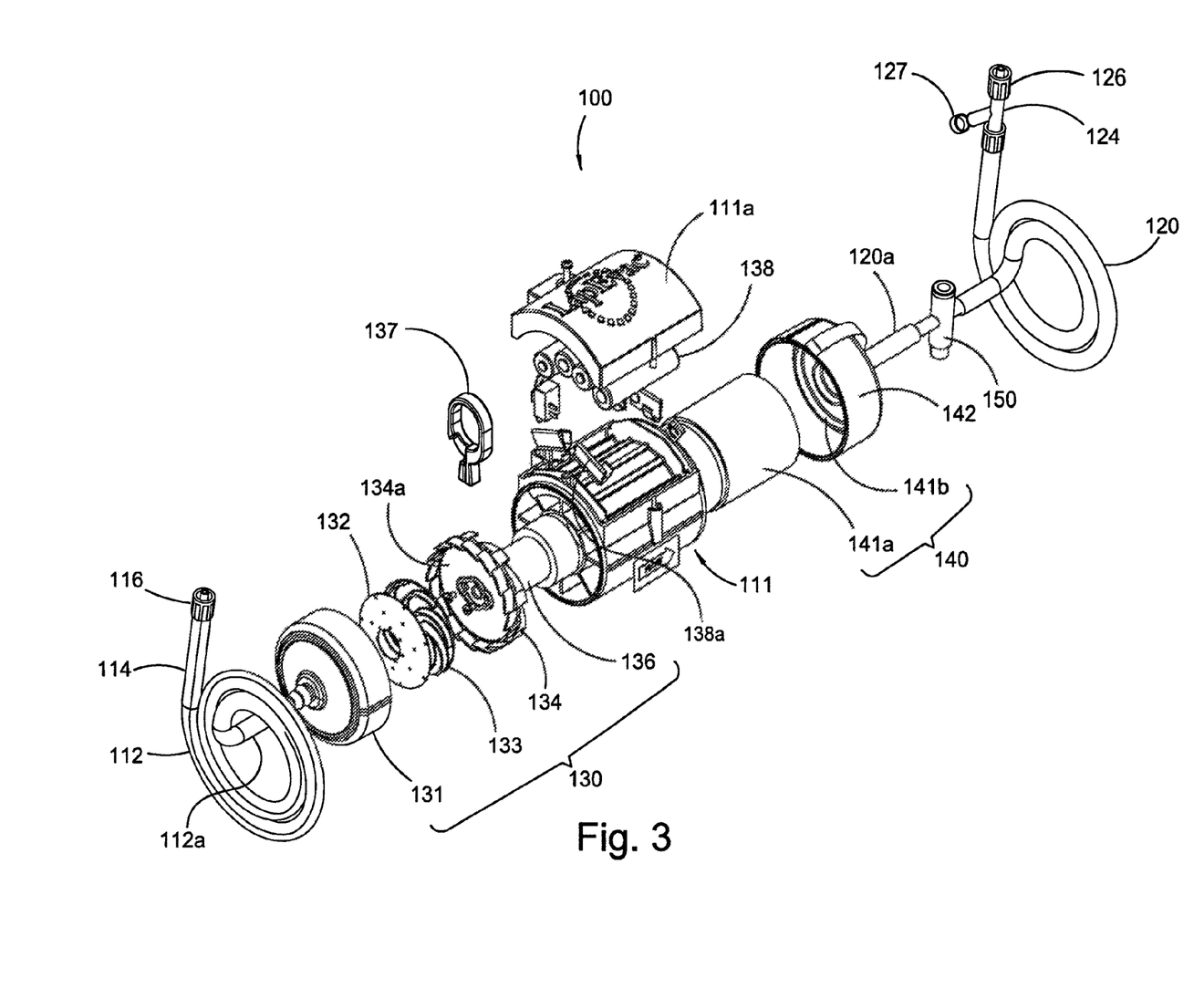
FIG. 3 is an exploded top perspective view of the disposable laparoscopic smoke evacuation system shown in FIG. 2.

FIG. 3 is an exploded top perspective view of lapevac 100. Inlet hose 112 is seen attached to inlet attachment 112a. Inlet assembly 130 includes inlet 131 which covers the fan or pump assembly to include impeller cover 132, impeller 133, fan 134, and fan mount 134a which are all attached to motor 136. Battery cover 111a covers battery (ies) 138 used to power motor 136. Although a plurality of AA batteries are shown in FIG. 3, persons of skill in the art will recognize that a single battery, various appropriate battery assemblies with different capacities, or alternative ac power sources may be used to provide power to motor 136.

Outlet 142 covers filter 140 positioned on the downstream side of fan assembly 130. In the preferred embodiment shown, filter 140 includes activated carbon media 141a as a prefilter plus ultra low particulate air (ULPA) filter 141b. Outlet attachment 120a extends from outlet 142 and is seen connected to t-tap valve 150. One end of outlet tube 120 is connected to t-tap valve 150, while the other end is connected to connector 124. A locking means 126 is positioned on at least one outlet of y-connector 124 to enable y-connector 124 to be securely attached to an additional component. In one embodiment, locking means 126 is a luer lock. Cap 127 is used to block an unused outlet of y-connector 124. In a preferred embodiment, locking means 116, such as a luer lock, may be positioned at the input end of inlet tube 112 as shown in FIGS. 2 and 3. Locking means utilized throughout the invention are defined as connections between two components that prevent the escape of vapor, liquid, or fumes from the connection itself. Examples of locking means are luer locks, tube connections in which one tube is inserted into another tube, interference fittings, Colder couplers and other connectors known to those skilled in the art that prevent the escape of fumes from a connection point.

Y-connector 124 receives filtered gas from lapevac 100. One of the two outlets of y-connector 124 can be connected to an insufflator while the second outlet can be connected to a second inlet into the abdominal cavity enabling gas filtered by lapevac 100 ("filtered gas") to be pumped into the abdominal cavity at two locations to help remove waste vapors generated by the laparoscopic surgical procedures.

Figure 3A:
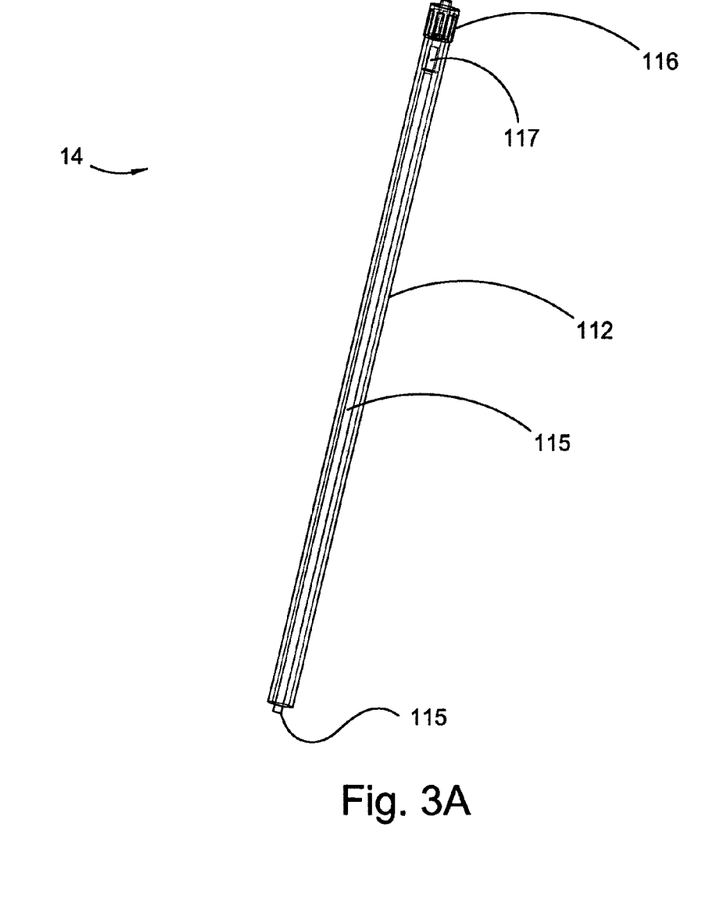
FIG. 3A depicts an enlarged view of the wick assembly of the present invention inserted into the inlet tube of the smoke evacuation system.

FIG. 3A depicts an enlarged view of wick assembly 114 incorporated into inlet tube 112. Inlet tube 112 is cut way to more clearly show wick 115. Luer lock 116 is shown at the inlet end of inlet tube 112.

Figure 4:
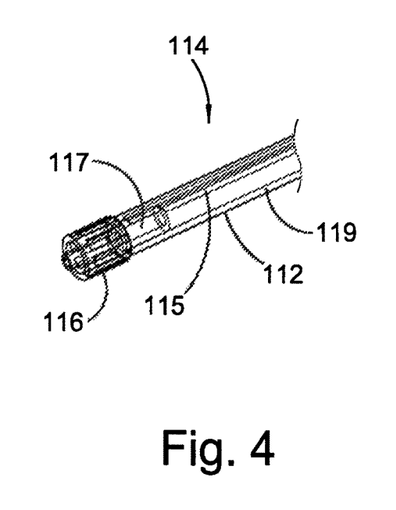
FIG. 4 is a top perspective view depicting the components of the wick assembly of the present invention in an assembled condition.

FIG. 4 is a top perspective view depicting the components of wick assembly 114 joined together in an assembled condition. Luer lock 116 is shown at the inlet end of inlet tube 112. Interference fitting 117 ("fitting 117") is attached to luer lock 116 and wick 115. Wick assembly 114 is inserted into inlet tube 112 and held in place by the friction of interference fitting 117 against the inner wall of inlet tube 112. Wick 115 is in the form of a strand or filament that extends into inlet tube 112. Preferably, wick 115 is fabricated from a hydrophilic material such as polyvinyl alcohol (PVA) or cotton. Wick 115 is sized with a diameter small enough to allow sufficient space for airway 119 between wick 115 and inner wall of inlet tube 112 to form a passage to allow smoke, air and other fluids to be easily drawn into inlet tube 112 and pass through filter 140 of lapevac 100 to outlet tube 120 in the form of filtered gas. By hydrophilic is meant the property of attracting and to at least some extent absorbing liquids and fluids.

Figure 4A:
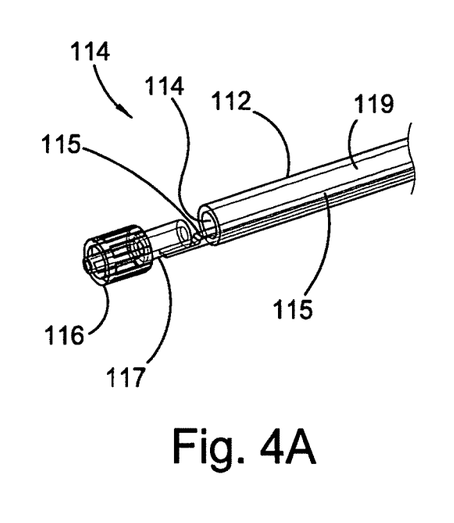
FIG. 4A is a top perspective view of a partially disassembled wick assembly.
Figure 4B:
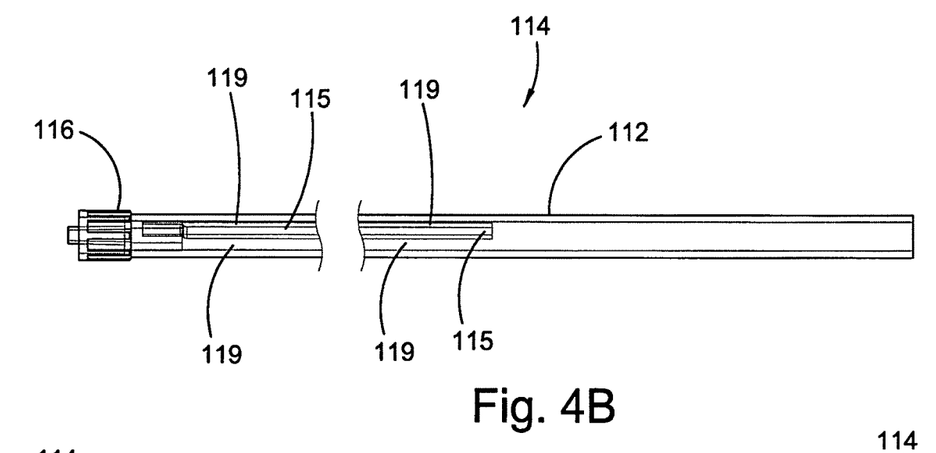
FIG. 4B is a side view of the assembled wick assembly of the present invention.

FIG. 4A is a top perspective view of partially disassembled wick assembly 114. Fitting 117 is attached to luer lock 116 and inserted into inlet tube 112. Luer lock 116 or other locking means used should be hollow in order to allow the flow of fluid, including vapors and gases, into and through inlet tube 112. Similarly, fitting 117 should also be hollow to allow for sufficient air flow to move incoming vapor and gas without taxing lapevac 100. Wick 115 is attached to fitting 117 and the luer lock-fitting-wick assembly is inserted into inlet tube 112. FIG. 4B is a side view of wick assembly 114 showing more clearly fitting 117 and wick 115 within inlet tube 112 and airway 119.

Figure 5:
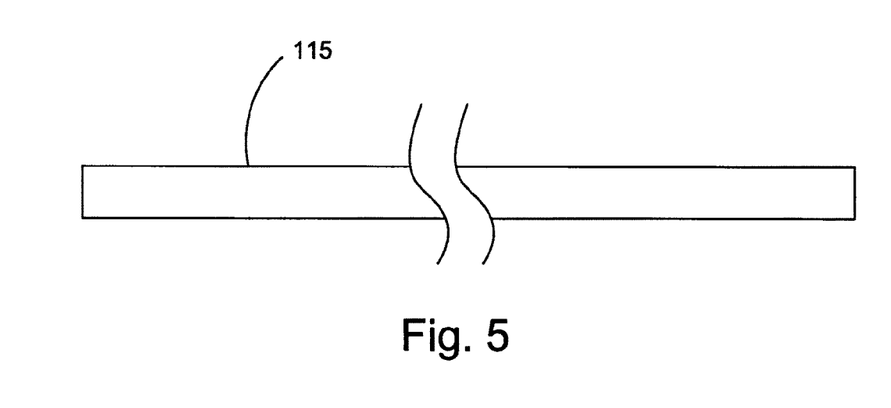
FIG. 5 is a side view of the wick component of the wick assembly of the present invention.
Figure 5A:
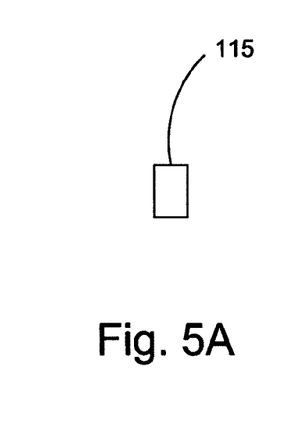
FIG. 5A is an end view showing one embodiment of the wick depicted in FIG. 4.
Figure 5B:
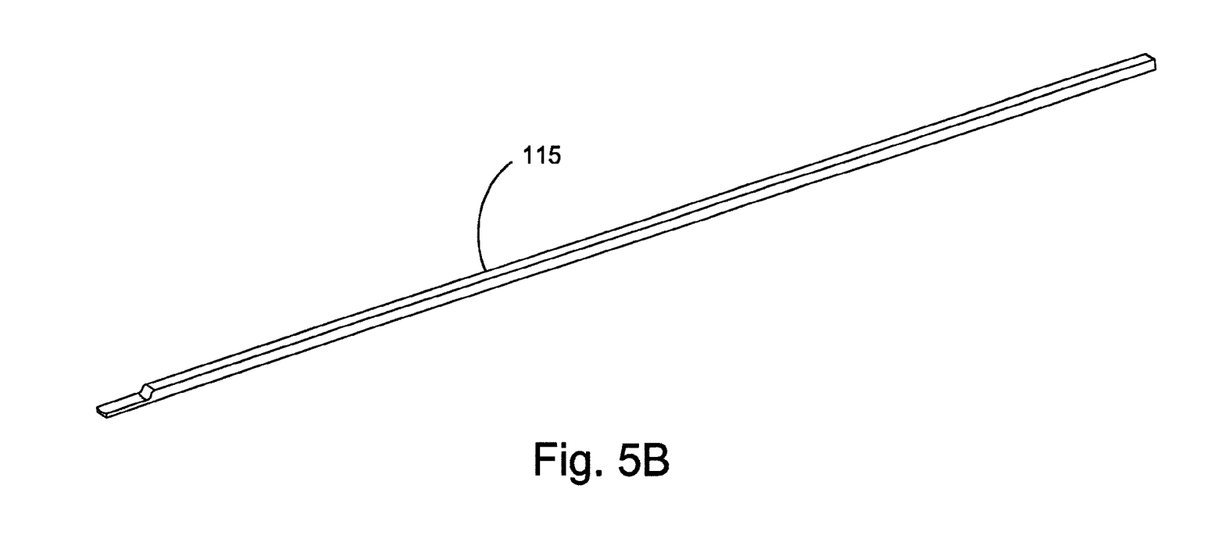
FIG. 5B is an isometric view of the wick shown in FIG. 4.

FIG. 5 is a side view of wick 115 fabricated from PVA. In the embodiment shown, wick 115 is about 20 inches long. FIG. 5A is an end view of wick 115 in which wick 115 possesses a rectangular cross section with a width of about 0.12 inches and a height of about 0.08 inches. FIG. 5B is an isometric view of wick 115. PVA is one of the preferred materials for fabricating wick 115. When dry it is rigid hydrophilic foam. In the presence of water or humidity it becomes soft and flexible with good chemical resistance and good water absorption properties.

Lapevac 100 is used during laparoscopic surgery to keep the field of view while performing surgical procedures. The inflation creates space within the cavity thereby making it easier to perform surgery. A separate insufflator inflates the abdominal cavity (or other cavity) by pumping air or other gas (es) into the abdominal cavity. To remove surgically generated smoke and other vapors, lapevac 10 removes smoke and other vaporous waste into inlet tube 112 through filter 140 and out outlet tube 120 as filtered gas. The second or downstream end of outlet tube 120 is attached to a hollow channel inserted into the abdominal cavity and to the insufflator by means of connector 124. Using this system, a recirculating stream of filtered gas or air enters the abdominal cavity as the smoke and waste filled vapors are removed to keep the abdominal cavity under a relatively constant inflation pressure.

Although lapevac system 100 is effective in maintaining cavity inflation pressure, one problem that occurs during its operation is the clogging of inlet tube 112 and filter 140 by solid waste, water and humidity carried out of the abdominal cavity by the incoming waste stream. Because the cavity is moist and may be heated above normal temperature by some surgical procedures such as cauterization, surgical wastes can be driven off the cavity wall and internal organs in the form of particles, vapor, and liquids from broken cells and tissues. In addition, vapors within the cavity itself can be drawn into the waste stream.

Because it is hydrophilic, wick 115, attracts and retains the solid moist waste and the aqueous liquid waste that is drawn into inlet tube 112. Because it is sized to allow for a large airway 119 between the inner wall of inlet tube 112 and wick 115, relative to the size of wick 115, wick assembly 114 allows waste stream vapors and gases to move without substantial additional restriction to filter 140. A preferred length of wick 115 is about 20 inches as this provides sufficient length for exposing the waste stream to the hydrophilic attraction of wick 115. In addition, the preferred rectangular shape provides more surface area to attract and hold waste particles and vapors than supplied by a round cylindrical shape.

It will be recognized that wick assembly 114 is also effective with passive laparoscopic filtration systems. A passive laparoscopic filtration system lacks the fan to actively pull waste vapors from the abdominal cavity, but instead relies on pressure supplied by the insufflator to push surgical waste through an inlet and wick assembly and filters.

Another problem that may occur during laparoscopic surgery is the insufficient removal of waste vapor from the cavity and stratification of water vapor in the cavity which can lead to visualization problems for those observing the procedures within the abdominal cavity. This waste vapor can be purged by means of a two-way relief valve 150 placed in the filtered gas outlet path within outlet tube 120. Relief valve 150 provides the user with the ability to accelerate clearing and/or removal of stratified laparoscopic filtration waste vapor by opening a divert path while blocking the recirculating filtered gas through the normal outlet path back to the cavity. This diversion provides a sudden pressure change by supplying a rapid evacuation capability.

Figure 6A:
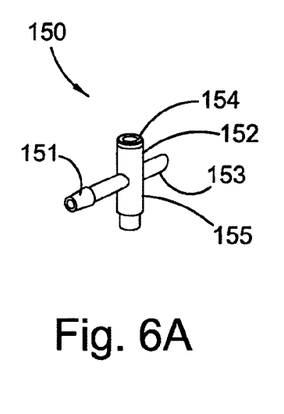
FIG. 6A is an isometric view of one embodiment of the two-way valve of the present invention in the divert mode.
Figure 6B:
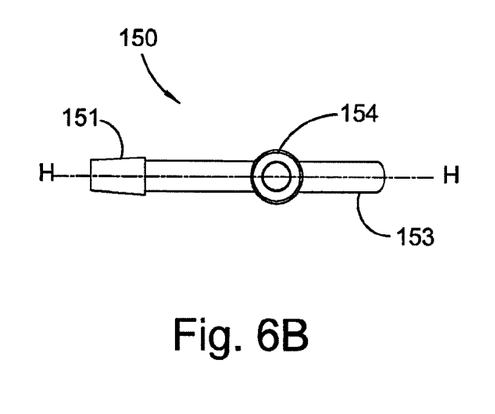
FIG. 6B is a top view of the two way outlet valve of the present invention in the divert mode.
Figure 6C:
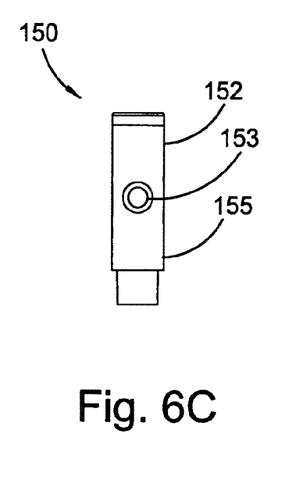
FIG. 6C is a side view of the two-way outlet valve from the side facing the outlet port in the divert mode.

FIGS. 6A-D show t-tap two way valve 150 ("valve 150") configured in the divert mode. FIG. 6A is an isometric view of valve 150 showing valve inlet 151, divert 152, outlet 153, and barrel housing 155. FIG. 6B is a top view of valve 150. FIG. 6C is a side view of valve 150 taken from the side facing outlet 153. It can be seen that in the divert mode, outlet 153 is closed.

Figure 6D:
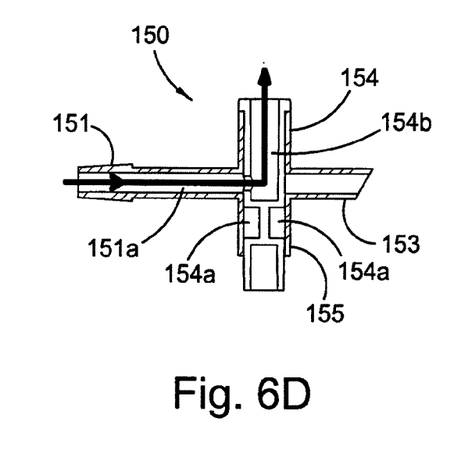
FIG. 6D is a cross section of the two-way valve taken along line H-H in FIG. 5B in the divert mode.

FIG. 6D is a cross section of valve 150 taken along line H-H in FIG. 6B. The arrow shows fluid flow along valve inlet 151 and through divert 152. Valve barrel 154 ("barrel 154") sits within divert 152 and extends past inlet 151 and outlet 153 into barrel housing 155. In the divert mode shown, barrel passages 154a are positioned below and blocked from the fluid pathway shown by the arrows. Thus, the filtered gas from lapevac 100 is diverted through barrel channel 154b and out divert 152 thereby relieving the back pressure situation.

Figure 7A:
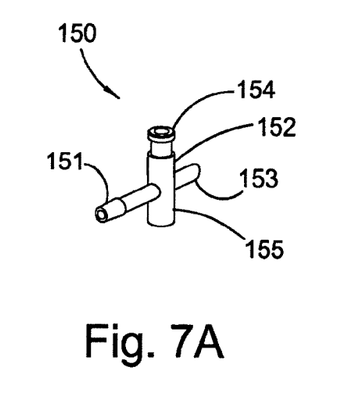
FIG. 7A is an isometric view of the two-way valve showing the valve barrel in the open (flow through) mode.
Figure 7B:
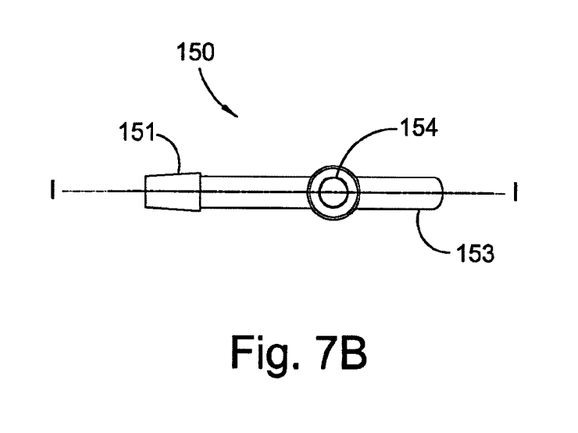
FIG. 7B shows a top view of the two-way valve in the open mode.
Figure 7C:
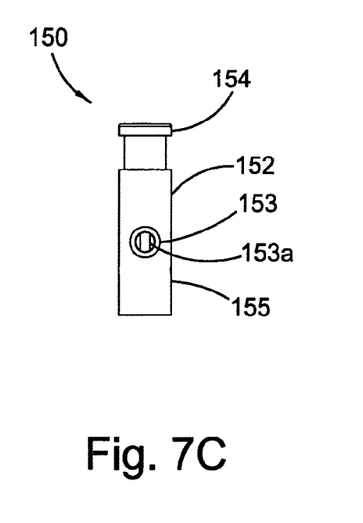
FIG. 7C is a side view of the two-way valve in the open mode facing the side of the outlet showing the open channel to the valve outlet.

FIGS. 7A-D depict t-tap two-way valve 150 configured in the flow through mode allowing filtered gas to return to the abdominal cavity. FIG. 7A is an isometric view of valve 150 showing barrel 154 extending from the top of divert 152. FIG. 7B shows a top view of valve 150 in the open position. FIG. 7C is a side view facing the side of outlet 153 in which is seen the pass through channel open to outlet 153.

Figure 7D:
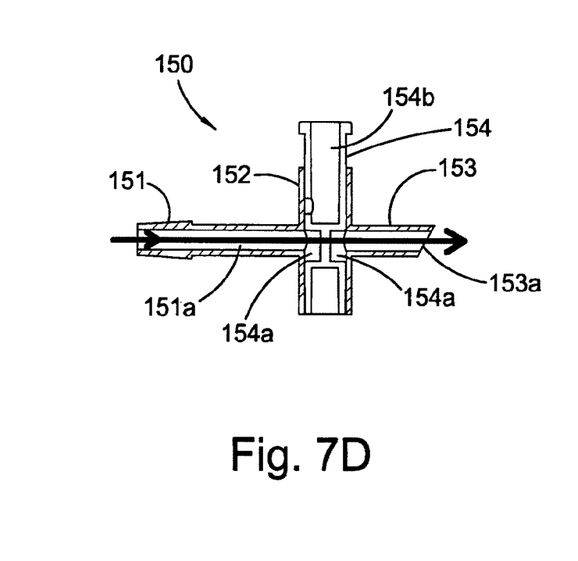
FIG. 7D is a cross section of the two-way valve taken along line I-I in FIG. 6B showing the channel configuration when the valve is in the open mode.

FIG. 7D is a cross section of valve 150 taken along line I-I in FIG. 7B showing the channel configuration when valve 150 is in the open mode. Barrel 154 is shown extended above the top edge of divert 152. This places barrel passages 154a into channel 151a (simultaneous alignment with inlet 151 outlet 153) and blocks entrance into divert 152. Filtered gas then exits through outlet 153 into outlet tube 120 (not shown in FIG. 7D) and into the abdominal cavity.

Figures 8A, 8B, 8C:
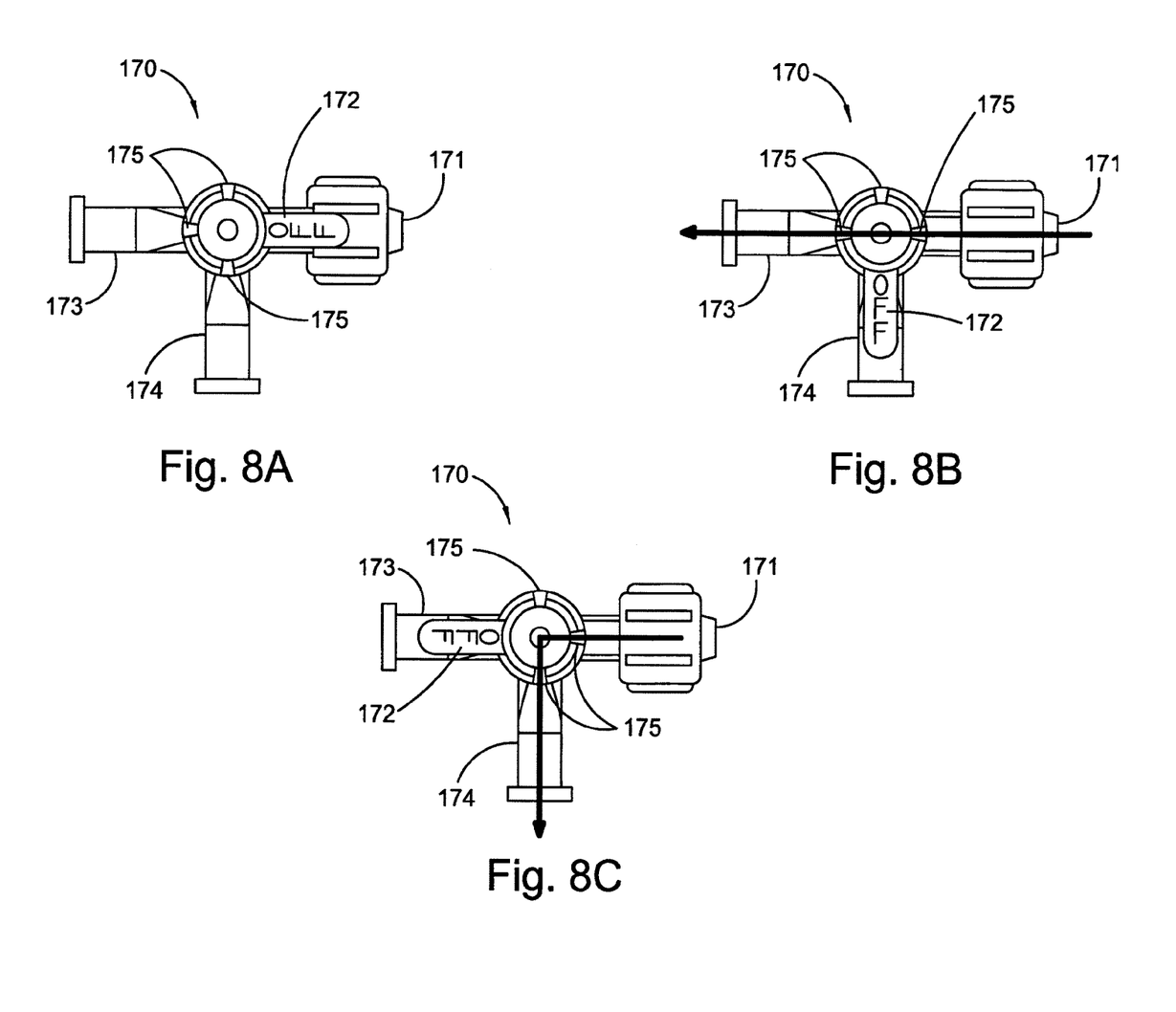

FIG. 8A is a top view of a second embodiment of the two-way divert valve, namely stopcock valve 170 ("valve 170"), in the closed or blocking mode. By blocking is meant that no fluid can enter valve 170. FIG. 7B is a side view of valve 170. Rotor 172 is seen at the junction of inlet 171, divert 174, and outlet 173. Persons of skill in the art will recognize that rotor 172 comprises three fluid flow passages 175 within a housing (not shown) with two passages 175 on opposite sides of rotor 172 and the third passage 175 at right angles between the other two passages. In the closed (no flow) position, the blocked side, lacking a passage 175, faces inlet 171. This configuration closes the passage of filtered gas in any direction through valve 70. In the divert position, FIG. 8C, the blocked side is rotated to face outlet 173. In this configuration, filtered gas flows through divert 172. In the flow through mode, FIG. 8B, the blocked side is rotated to face divert 172, forcing the filtered gas to flow through outlet 73.

It is apparent that by positioning a two-way valve, such as valves 150 or 170, in outlet tube 120, the effects of back pressure from either the insufflator or unfiltered back flow from the abdominal cavity are reduced or eliminated. Filtered air can be diverted from the recirculating waste/filtered gas system until the visualization within the cavity is brought to acceptable conditions.

Thus, it is seen that the objects of the present invention are efficiently obtained, although modifications and changes to the invention should be readily apparent to those having ordinary skill in the art, which modifications are intended to be within the spirit and scope of the invention as claimed.

We claim:

1. A smoke removal apparatus comprising: a housing; inlet means for defining an inlet pathway for impure gas from a surgical cavity to said housing, wherein said inlet pathway comprises a closed central passageway, and wherein said inlet means include locking means for connecting said surgical cavity to said inlet pathway; filter means for filtering impurities from impure gas to form filtered gas; outlet means for defining an outlet pathway for said filtered gas from said housing to said surgical cavity; and a fan, for drawing impure gas from said surgical cavity, through said inlet means, and through said filter means to form said filtered gas and for driving said filtered gas through said outlet means into said surgical cavity, wherein said outlet means are adapted to a laparoscopic surgical instrument assembly;
a fitting, wherein said fitting contacts said inlet means; and
a hydrophilic wick extending from an inlet end of said inlet means, wherein said hydrophilic wick is inserted into said locking means of said inlet means, and wherein said friction fitting attaches to said hydrophilic wick and to said locking means so as to form a wick assembly comprising an airway between said inlet means and said hydrophilic wick of said wick assembly, and further wherein said wick assembly is held in place by friction from said contact.

2. The smoke removal apparatus of claim 1, wherein said hydrophilic wick is polyvinyl alcohol (PVA).

3. The smoke removal apparatus of claim 1, wherein said hydrophilic wick is cotton.

4. The smoke removal apparatus of claim 1, wherein said hydrophilic wick comprises a rectangular cross section.

5. The smoke removal apparatus of claim 1, further comprising a multi-outlet valve incorporated into said outlet means.

6. The smoke removal apparatus of claim 5, wherein said multi-outlet comprises a two-way outlet valve.

7. The smoke removal apparatus of as recited in claim 6, wherein said two-way relief valve is a t-tap valve.

8. The smoke removal apparatus of claim 6, wherein said two-way relief valve comprises a stop cock having two outlets.

9. The smoke removal apparatus of claim 1, wherein said filter means comprises a pre-filter.

10. An inlet means for a smoke removal apparatus comprising:
an inlet tube having an inlet end, a closed central passageway, and a hollow locking means attached to said inlet end;
a hydrophilic wick assembly, said hydrophilic wick assembly comprising:
a hydrophilic wick; and
a friction fitting attached to said hydrophilic wick, said friction fitting defining an orifice, wherein the hollow locking means is attached to said friction fitting, and wherein said friction fitting forms an attachment with said inlet end such that said wick of said hydrophilic wick assembly extends from said inlet end when inserted inside said inlet tube so as to form an airway between said inlet tube and said hydrophilic wick.

11. The inlet means as recited in claim 10, wherein said hydrophilic wick is composed of PVA or cotton.

12. The smoke removal apparatus of claim 1, wherein the hydrophilic wick is non-cylindrical.

13. The smoke removal apparatus of claim 12, wherein the hydrophilic wick is rectangular.

14. The smoke removal apparatus of claim 1, wherein the hydrophilic wick is about 20 inches in length.

15. The inlet means of claim 10, wherein the hydrophilic wick is non-cylindrical.

16. The inlet means of claim 15, wherein the hydrophilic wick is rectangular.

17. The inlet means of claim 10, wherein the hydrophilic wick is about 20 inches in length.

* * * * *